United States Patent [19]

Shirota

[11] Patent Number: 5,112,224
[45] Date of Patent: May 12, 1992

[54] DENTAL DETECTION APPARATUS FOR POSITION OF ROOT APEX

[75] Inventor: Kazunari Shirota, Tokyo, Japan

[73] Assignee: Shirota Denki Rozai Kabushiki Kaisha, Tokyo, Japan

[21] Appl. No.: 667,995

[22] Filed: Mar. 12, 1991

[30] Foreign Application Priority Data

Jul. 13, 1990 [JP] Japan ............... 2-75018[U]

[51] Int. Cl.⁵ .................. A61C 1/00; A61C 5/02; A61B 5/103
[52] U.S. Cl. ................... 433/27; 433/224; 128/776
[58] Field of Search ............ 433/27, 32, 72, 224; 128/776, 777

[56] References Cited

U.S. PATENT DOCUMENTS

| | | | |
|---|---|---|---|
| 3,916,529 | 11/1975 | Mousseau | 433/224 X |
| 3,993,044 | 11/1976 | McGuffin | 433/224 X |
| 4,193,408 | 3/1980 | Fujino | 128/776 X |
| 4,243,388 | 1/1981 | Arai | 433/224 X |
| 4,353,693 | 10/1982 | Dery et al. | 433/224 X |
| 4,526,179 | 7/1985 | Salesky | 128/776 |

*Primary Examiner*—Robert P. Swiatek
*Assistant Examiner*—Nicholas A Lucchesi
*Attorney, Agent, or Firm*—Browdy and Neimark

[57] ABSTRACT

A dental detection apparatus for the position of a root apex comprises two oscillators for generating the currents having two different frequencies passing between a single electrode contacting to a patient's body and a reamer, a differential ampliifer for detecting the difference ΔV of the respective impedance variations of these currents, a direct current amplifier for amplifying the output of the differential amplifier to input to a meter, a comparator for connecting the output side to a two contact analog switch, the input side of the comparator being connected to the OUT of the direct current amplifier, a binary up/down counter for switching the input frequencies to the count down condition or the count up condition by the switching operation of the two contact analog switch, a D/A converter for connecting the output side to the differential amplifier so as to operate the offset of the differential amplifier, while the input side being connected to the OUT of the binary up/down counter, and an automatic calibration switch for passing the frequency signal transmitted from one of the two oscillators by ON operation to the binary up/down counter through the two contact analog switch.

1 Claim, 2 Drawing Sheets

DENTAL DETECTION APPARATUS FOR POSITION OF ROOT APEX

BACKGROUND OF THE INVENTION

1. Field of the Invention

This invention relates to a dental detection apparatus for locating the position of the final end (root apex) of a root canal by means of determining the impedance variations between a reamer and a single electrode interval during dental treatment of root canals by dentists.

More specifically, the dental detection apparatus for locating the position of a root apex, of the present invention, is based on providing an alternating current with two different frequencies between a reamer inserted in the root canal and a single electrode contacting the mucosa of the patients buccal cavity, and thereafter obtaining the corresponding impedances to the two frequency signals as the reamer approaches the root apex in order to detect the position of the root apex by measuring the difference between these impedance variations.

2. Description of the Prior Art

The dental detection apparatus for locating the position of a root apex according to the invention is based upon on the difference of the impedance variations corresponding to two different frequency signals in order to accurately detect the position of the root apex, even though the internal portion of the root canal is wet, or a nerve is left in the internal portion of the root canal and sanious pus is present.

Prior art devices of the type shown in FIG. 1 however, detect the position of the root apex with moisture, nerve and sanious pus in the root canal, with a meter indicating the position of the root apex according to the condition of the root canal. In such devices, a reamer is inserted into the root canal, and a volume adjustment made to set the reading of the meter at a required position (standard position) while continuing insertion of the reamer.

In the prior art device shown in FIG. 1, a reamer 2 is electrically connected to a detection apparatus A and then the reamer is inserted into a root canal 10 of a tooth 1 being treated for a patient to detect the position of the root apex. An indicator N on meter M indicates the position of the root apex on apparatus A by the amount it deflects in the direction of the position described as APEX as the reamer is inserted into the root canal and the condition of the root canal is adjusted for by manipulating dial D. Adjusting the reading N to the standard position described as ADJ is made by turning the dial D of a variable resistor incorporated in the body a. Then, while manipulating dial of and observing the reading N of the meter M, the reamer 2 is inserted and the location of root apex within the root canal 10 is made. When the reading N reaches the position of APEX, thereby indicating the location of the root apex the dental treatment is stopped.

Every time the dental treatment is made with such a prior art device, the reading N of the meter M must be manipulated by dial D to be set at the standard position. This operation is a complicated procedure.

SUMMARY OF THE INVENTION

The present invention is intended to solve the problem of prior art devices as shown in FIG. 1. The object of the present invention is to provide a new apparatus for automatically adjusting the reading N to the standard position with a switch which eliminates the need for volume adjustment of prior art devices and permits the reading N in the meter M corresponding to the individual condition within the root canal 10 of the patient's tooth 1 by only inserting reamer 2 into the root canal 10 and using switch S to set the readings to reflect the condition of the root canal. This is achieved by the power switch S on in the dental detection apparatus A substituting to locate the position of a root apex, setting the single electrode 3 in the apparatus A on the mucosa of the patient's buccal cavity and inserting the reamer 2 electrically connected to the apparatus A into the root canal 10 of the patient's tooth 1.

The present invention in its preferred mode, provided a dental detection apparatus for the position of a root apex comprising: two oscillators for generating the currents having two different frequencies passing through the reamer and the patient's body to a single electrode contacting a patient's body, a differential amplifier for detecting the difference $\Delta V$ of the respective impedance variations of the currents activated by passage through the body, a direct current amplifier for amplifying the output of the differential amplifier to input to a meter, a comparator for connecting the output side of the differential amplifier to a two contact analog switch, the input side of the comparator being connected to the OUT of the direct current amplifier, a binary up/down counter for switching the input frequencies to the count down condition or the count up condition by the switching operation of the two contact analog switch, D/A converter for connecting the output side of the up/down counter to the differential amplifier so as to operate the offset of the differential amplifier, while the input side of the up/down counter being connected to the OUT of the binary up/down counter, and an automatic calibration switch for passing the frequency signal transmitted from one of the two oscillators by ON operation to the binary up/down counter through the two contact analog switch thereby permitting the meter reading to reflect the condition of the root canal and locate the root apex by further inserting the reamer.

DETAILED DESCRIPTION OF PREFERRED EMBODIMENT

Figure 1:
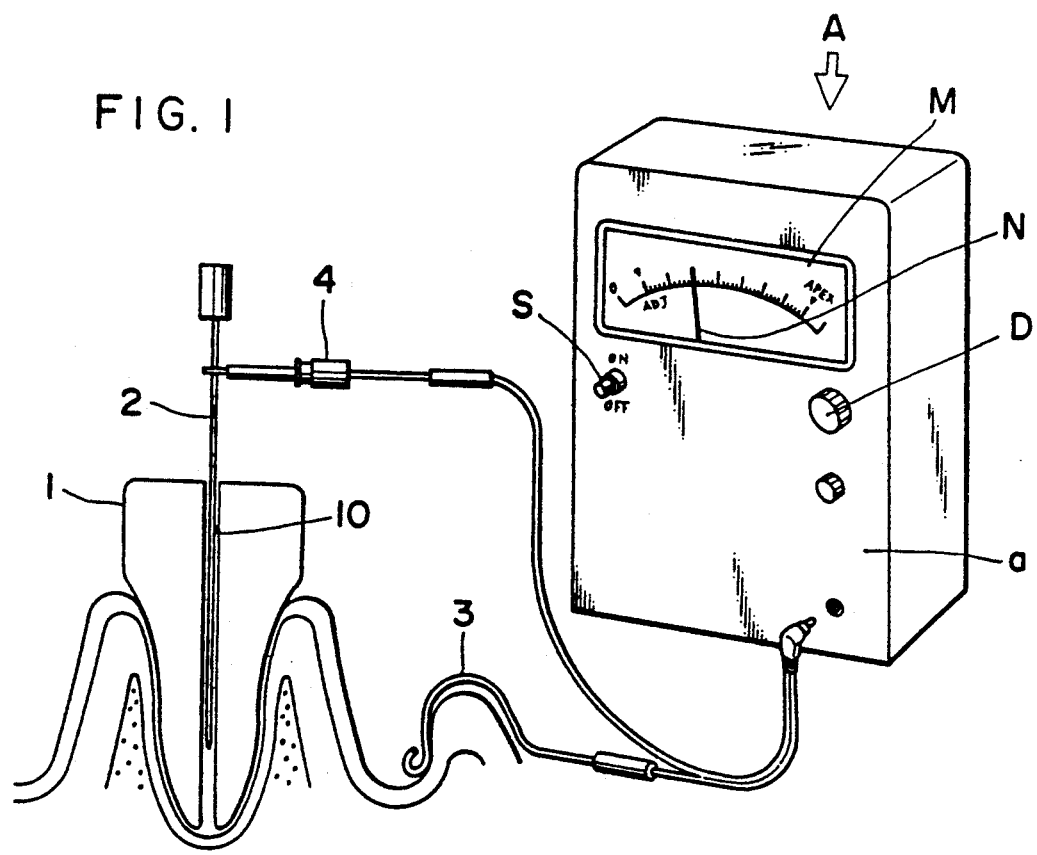
FIG. 1 is a explanatory drawing of a prior art apparatus for detecting the position of a root apex.

A detailed description of a preferred embodiment is given with reference to the drawings, wherein the same numerals are used in the different drawings including the drawing of the prior art apparatus to identify identical parts in both the preferred embodiment and the prior art apparatus.

Figure 2:
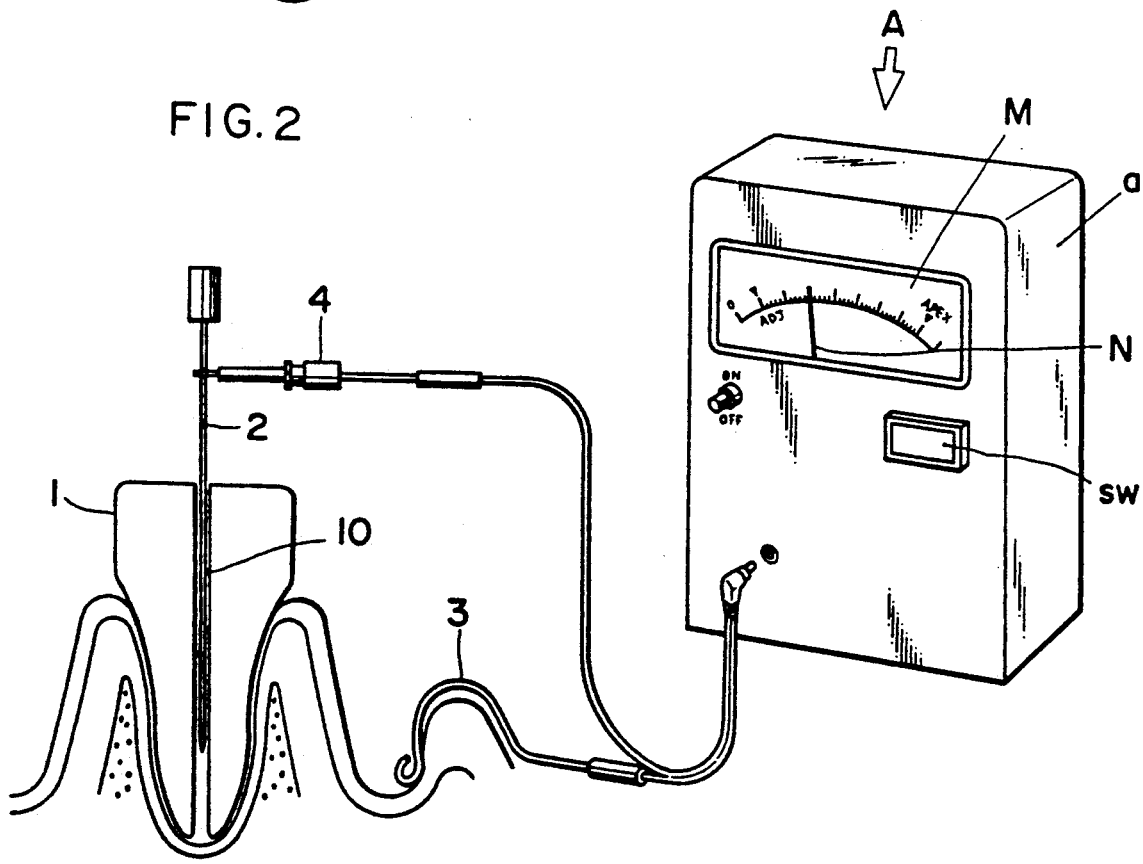
FIG. 2 is perspective drawing of the preferred embodiment of the present invention to detect the position of a root apex in a tooth.

FIG. 2 shows the preferred embodiment of the present invention of a dental detection apparatus for detecting the position of a root apex of a tooth. Referring to the drawing, a designates the body of the dental detection apparatus A for locating the position of a root apex, 1 a patient's tooth to be treated, 2 a reamer inserted into the root canal 10 of the tooth 1, 3 a single electrode set on the patient's lip, 4 a holder for electrically/connecting a pulse generator in the body a and the reamer 2, M a display meter installed in the body a for indicating the position of a root apex, N a display reading, and SW a switch for setting the standard position to zero or to automatically adjust the reading N of the meter M to read the condition within the root canal 10 at starting insertion of the reamer.

Figure 3:
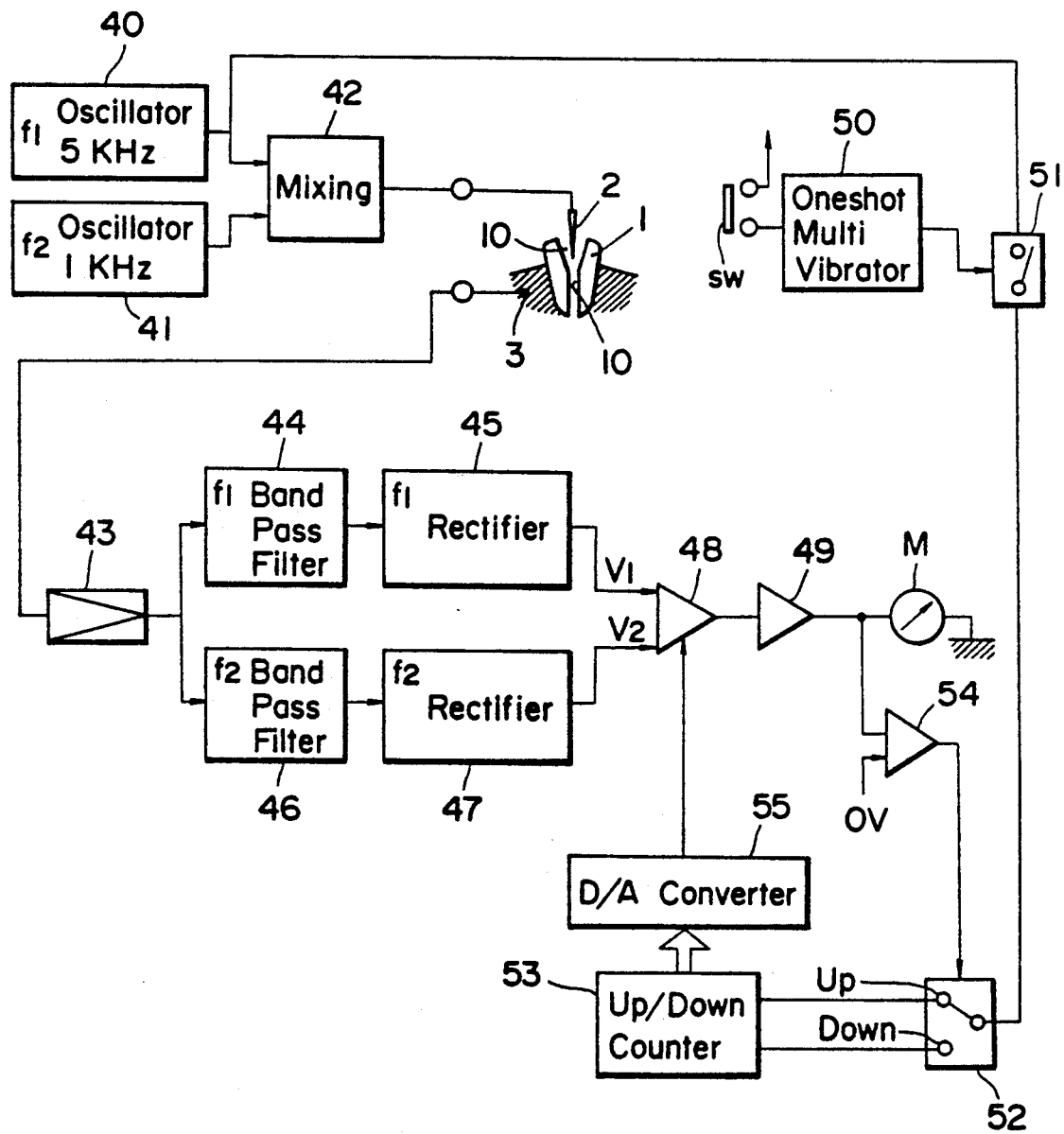
FIG. 3 is a block diagram of the elements comprising the preferred embodiment of the present invention of the dental detection apparatus for detecting the position of a root apex.

FIG. 3 is schematic drawing and block diagram of the dental detection apparatus for locating the position of a root apex as discussed above. Referring to this drawing, 40 designates an oscillator transmitting a frequency signal of 5 KHz, 41 an oscillator transmitting a frequency signal of 1 KHz, 42 a mixing circuit for mixing two kinds of waveform signals transmitted from the oscillators 40 and 41 and sending the mixed signal to the reamer 2, 43 an amplifier for amplifying the micro electric current which has been attenuated by flowing from the reamer 2 through the single electrode 3 by way of the root canal 10 of the tooth 1, 44 a bandpass filter taking out only the current having the frequency of 5 KHz from the amplified current through the amplifier 43, 45 a rectifier for transforming the current passing through the filter 44 into a direct current, 46 a band-pass filter taking out only the current having the frequency of 1 KHz from the current passing through the amplifier 43, 47 a rectifier for transforming the current passing through the filter 46 into a direct current, 48 a differential amplifier for outputting the difference ΔV between the voltage V1 and V2 corresponding to two currents resulting from these two rectifiers 45 and 47, 49 a direct current amplifier for amplifying the current of this difference ΔV, and M a meter for displaying the current of the difference ΔV output from the direct current amplifier 49, respectively. These are set as shown in the block diagram of FIG. 3 and installed within the body a, and when the reamer 2 is inserted into the root canal 10 of the tooth by this procedure, the difference between respective impedances of the currents having two different frequencies passing through the single electrode 3 from the reamer 2 is set and displayed by reading N in the meter M installed in the body a.

At that time when the reamer 2 is pushed into the root canal 10 of the tooth 1 and the automatic calibration switch activated, the current passing through the single electrode 3 from the reamer 2 reads the conditions within the root canal 10 such as moisture, nerve, sanious pus or the like. As a result, the meter M detects this difference and sets the process for moving the reading N corresponding to the condition within the root canal 10. Thereafter with the calibration switch off, the dental treatment with locating the root apex with the reamer within the root canal 10 is done. At the time when the reamer 2 is pushed into the root canal 10 of the tooth 1, it is necessary to adjust the reading N deflected according to the conditions within the root canal 10 to the standard position, but the variable resistor activated by the operation of a dial D incorporated in the prior art device shown in FIG. 1 has been eliminated by the automatic calibration switch circuit.

The process of adjusting the reading N of the meter M deflected by reading the condition within the root canal 10 to the standard position is automatically carried out by operating the automatic calibration switch SW installed in the body a.

This is achieved by the automatic calibration switch circuit shown in FIG. 3, where 50 designates a one shot (one shot multi-vibrator) activated to generate one single pulse by pushing the automatic calibration switch SW on. This simply generates one single pulse by setting the trigger. The period of time generating a pulse is set to be one second.

51 designates an analog switch which is activated to on only when the pulses are generated from the one shot 50.

52 designates a two contact analog switch control which is activated on while the analog switch 51 is processed to switch on. The two contacts are connected to one contact for activating a binary up/down counter 53 to count up and the other contact for activating the same to count down, respectively. The analog switch 52 is an integrated circuit (IC) for selecting and switching to process an analog value forwarded from a comparator 54, and it is processed to select the contact DOWN at a down side when the analog value forward from the comparator 54 is plus and to select the contact UP at an up side when the analog value forward from the comparator 54 is minus.

The input side of the comparator 54 is connected to a portion between the direct current amplifier 49 and the meter M so that the comparator 54 may watch whether a direct current amplifier 49 is out or not. The standard in the comparator 54 is set at 0 volt, and when the out of the direct current amplifier 49 is plus, the comparator 54 is set to give the output of the signal (the two value signals whether they are H or L) for selecting DOWN to the analog switch 52.

The binary up/down counter 53 is operated by switching the input frequency to the condition to be counted down or the condition to be counted up, and the switching of the process is automatically controlled by the two contact analog switch 52. OUT of the up/down counter is connected to the D/A converter 55 for converting a direct current to an alternating current, and is converted into an analog value by the D/A converter. The OUT from this D/A converter 55 is connected to the differential amplifier 48 to operate the offset of the differential amplifier 48.

The following is an explanation of the operation of the present invention. When the reading N of the meter M deflects according to the condition within the root canal 10 by pushing the reamer 2 into the root canal 10 of the tooth 1, the one shot 50 is operated by striking the automatic calibration switch SW. The analog switch 51 is closed by this procedure during the period of time when the pulses are generated and the current having a frequency of 5 KHz as an output from the oscillator 40 flows as a clock input of the binary up/down counter 53 through the two contact analog switch 52. In case the OUT of the direct current amplifier 49 is plus at this time, the analog switch 52 is operated so as to select the contact DOWN at the down side, and the binary up/down counter 53 counts down and sends out the input frequency to the D/A converter 55, and it operates the offset of the differential amplifier 48. When the OUT in both of the differential amplifier 48 and the direct current amplifier 49 leads to zero or exceeds at minus side beyond zero, the up and down movement of plus and minus after this time becomes a fine vibration by the one bit part of the resolution of the D/A converter 55 (for example, when it is the D/A converter of twelve bits, the resolution of 1/4096 of the standard voltage given to the D/A converter is given.) At the same time, the comparator 54 operates to move the offset of the differential amplifier 48 and the plus direct current amplifier 49 to the plus side as the analog switch 52 inputs the signal for selecting UP to the analog switch 52, the switch 52 carries out the operation for selecting the contact UP at the up side, and the binary up/down counter 53 membries the operation for counting up the input frequencies. The OUT of the direct current amplifier 49 moves to nearly to zero by repeating this operation.

Even though it is assumed that the binary up/down counter 53 is fully counted to the worst conditions MSB to LSB, it comes to 4096 steps at twelve bits. Therefore, 4096/5000 seconds are given to the clock of the binary up/down counter 53 of 5 KHz to get to zero point without fail. This means that one shot of one second is good enough.

When the period of time of the one single pulse as an output from the one shot 50 elapses, the analog switch 51 opens and by this procedure the binary up/down counter 53 stops its operation. At this time, as the analog switch 51 is opened, the clock of the oscillator 40 used in common as a clock of the binary up/down counter 53 is stopped. Therefore, the binary up/down counter 53 holds the final value and comes to hold the condition nearly to the memorized zero. As a result, when the reading N of the meter M deflects by inserting the reamer 2 into the root canal 10 of the tooth 1, and if the automatic calibration switch SW is struck, almost instantly, the operation for calibrating the deflection of the reading N and adjusting the reading N to the standard position is automatically done.

As mentioned above, the dental detection apparatus for locating the position of a root apex comprises two oscillators 40 and 41 for generating the currents having two different frequencies passing between the single electrode 3 contacting a patient's body and the reamer 2, the differential amplifier 48 for detecting the difference $\Delta V$ of the respective impedance variations of these currents, the direct current amplifier 49 for amplifying the output of the differential amplifier to input to the meter M, the comparator 54 for connecting the output side to the two contact analog switch 52, the input side of the comparator being connected to the OUT of the direct current amplifier 49, the binary up/down counter 53 for switching the input frequencies to the count down condition or the count up condition by the switching operating of the two contact analog switch 52, the D/A converter 55 for connecting the output side to the differential amplifier 48 so as to operate the offset of the differential amplifier 48, while the input side being connected to the OUT of the binary up/down counter 53, and the automatic calibration switch SW for passing the frequency signal transmitted from one of the oscillators 40 and 41 by ON operation to the binary up/down counter 53 through the two contact analog switch 52.

Therefore, the reading N of the meter M is automatically adjusted to the standard position due to a switch operation in case the reading N of the meter M deflects with correspondence to the individual condition within the root canal 10 of the patient's tooth 1, by putting the power switch on in the dental detection apparatus A for locating the position of a root apex, setting the single electrode 3 in the apparatus A on the mucosa of the patient's buccal cavity and inserting the reamer 2 electrically connected to the apparatus A into the root canal 10 of the patient's tooth 1.

What is claimed is:

1. A dental detection apparatus for locating the position of a root apex of a tooth in a body of a dental patient comprising:

a reamer for insertion into a root canal of said tooth;

a single electrode contacting said body of said dental patient near said tooth;

two oscillators which generate currents having two different frequencies;

said oscillators connected to said reamer;

said currents passing through said reamer and said body as attenuated currents to said single electrode;

a differential amplifier connected to said single electrode for detecting a difference $_DV$ of respective impedance variations in said attenuated currents;

a direct current amplifier connected to said differential amplifier for amplifying the output of said differential amplifier;

a meter connected to said direct current amplifier for displaying the output of said direct current amplifier;

a comparator connected to an output side of said direct current amplifier and to an input side of a two contact analog switch, a binary up/down counter connected to an output side of said two contact analog switch for switching said counter to an up or to a down condition depending on an input frequency of said two contact analog switch;

a direct current/alternating current converter connected to an output side of said binary up/down counter;

an output side of said direct current/alternating current converter connected to said differential amplifier to create an offset of said differential amplifier;

an automatic calibration switch connected to one of said two oscillators for passing a frequency signal from said one of said two oscillators when switched on to said binary up/down counter through said two contact analog switch;

wherein switching on said automatic calibration switch when said reamer is first inserted into said root canal determines a condition of said root canal displayed on said meter and when thereafter switching off said automatic calibration switch enables further insertion of said reamer to compensate for said condition and locate said root apex by display on said meter.

* * * * *